July 3, 1956 G. DE RUITER Plant Pat. 1,493
ROSE PLANT
Filed Aug. 9, 1955
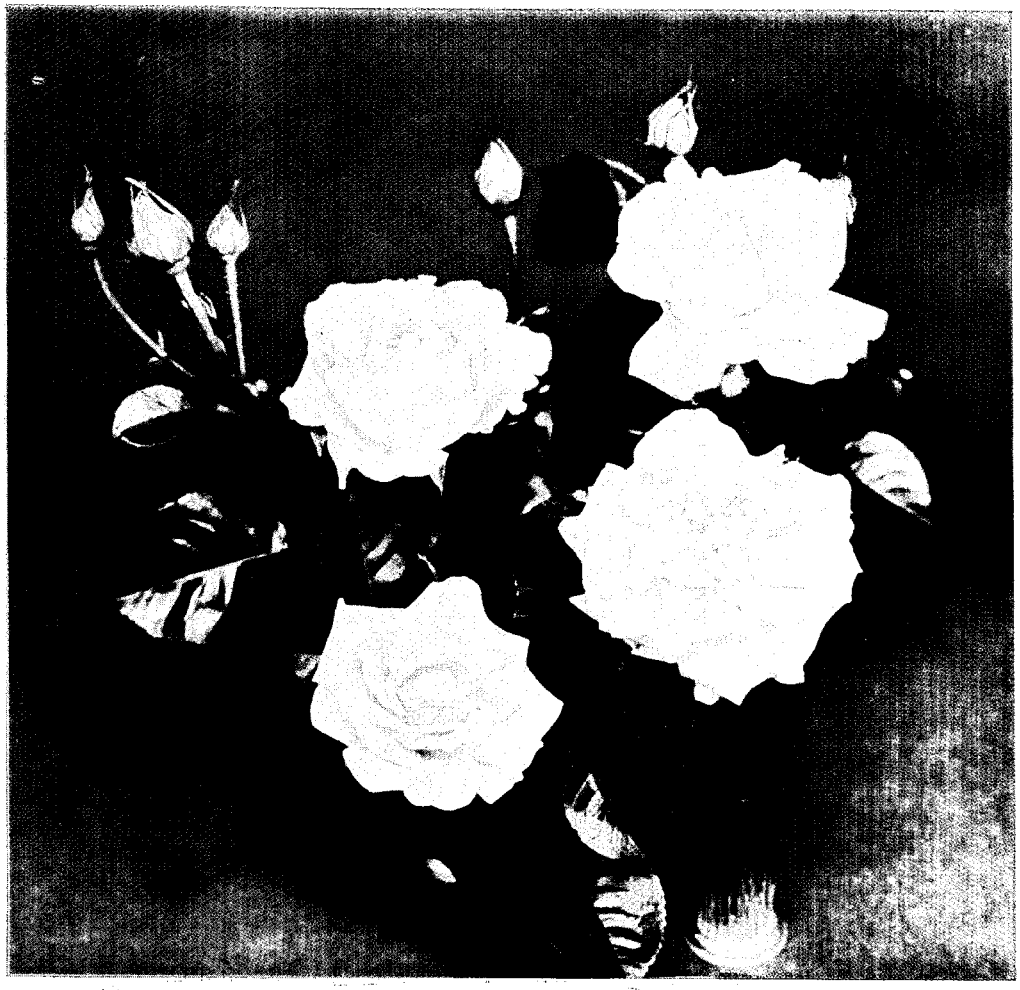
Inventor:
Gerrit de Ruiter
By: Robb & Robb
Attorneys.

United States Patent Office

Plant Pat. 1,493

Patented July 3, 1956

1,493

ROSE PLANT

Gerrit de Ruiter, Hazerswoude, Netherlands, assignor to Ilgenfritz Nurseries, Inc., Monroe, Mich., a corporation of Michigan Application August 9, 1955, Serial No. 527,433

1 Claim. (Cl. 47—61)

The present invention relates to a new and distinct variety of rose plant of the hybrid tea class, which was originated by me by crossing an unnamed and unpatented seedling derived from "Orange Triumph" (unpatented) X "Golden Rapture" which is known in Europe as "Geheimrat Duisberg" (unpatented) with the variety "Peace" (Plant Patent No. 591).

As the result of this breeding, I have produced a new rose variety which is particularly characterized as to novelty and distinctiveness by its hardiness, its leathery and glossy foliage, the fullness and distinctive color of its blooms and their habit of holding their color very well, and its very good resistance to blackspot and mildew.

The foregoing characteristics and distinctions definitely differentiate my new variety from its parents, as well as from all other varieties of its class of which I am aware, and asexual reproduction of the new variety by budding, as performed by me in Holland, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart issued by the British Color Council in collaboration with the Royal Horticultural Society, except where general color terms of ordinary dictionary significance are obvious:

Type: Hardy; tall; outdoor; seedling; for cut flowers and for garden decoration.

Class: Hybrid tea.

Breeding: Seedling.

*Seed parent.*—An unnamed seedling of "Orange Triumph" X "Golden Rapture" (known as "Geheimrat Duisberg" in Europe).

*Pollen parent.*—"Peace."

Propagation: Holds its distinguishing characteristics through succeeding propagations by budding.

FLOWER

Locality where grown and observed: Monroe, Michigan, U. S. A.

Continuity: Continuous.

Fragrance: Moderate. Nature—spicy.

Flowers borne: In irregular, rounded, pyramidal clusters; on strong stems of medium length.

Quantity of bloom: Abundant, outdoors.

Bud:

*Peduncle.*—Medium length; heavy; erect; stiff; with numerous Red prickles. Color—Green-Bronze.

*Before calyx breaks.*—Size—medium. Form—pointed; with foliaceous appendages on the surface of the bud; with much-cut foliaceous parts extending beyond the tip of the bud. Color—Scheele's Green, Plate 860/2.

*As calyx breaks.*—Color—Scarlet, Plate 19/2.

*As first petal opens.*—Size—large. Form—pointed. Color: Outside—Rose Bengal, Plate 25/3; inside—Rhodamine Pink, Plate 527.

*Opening.*—Opens up well.

Bloom:

*Size (when fully open).*—Large; from 4½ inches to 5 inches.

*Petalage.*—Double; from 78 to 85 petals; arranged irregularly.

*Form.*—Full at first, but becoming open; petals being at first tightly rolled outward, but becoming loosely rolled outward later at maturity.

Petals:

*Texture.*—Thick; with inside velvety and outside satiny.

*Shape.*—Outside—ovate, with 1 notch. Intermediate—ovate, with 1 notch. Inside—ovate, with 1 notch.

This description of a newly opened flower was made from a rose grown outdoors in the month of June, at Monroe, Michigan, U. S. A.:

*Color.*—Outer petal: Outside surface—Rose Bengal, Plate 25/3; inside surface—Solferino Purple, Plate 26/2. Intermediate petal: Outside surface—Tyrian Rose, Plate 24/3; inside surface—Rose Bengal, Plate 25/2. Inner petal: Outside surface—Tyrian Rose, Plate 24/3; inside surface—Phlox Pink, Plate 625.

This description was made from a rose that was open for 3 days outdoors in the month of June, at Monroe, Michigan, U. S. A.:

*Color.*—Outer petal: Outside surface—Tyrian Rose, Plate 24/3; Inside surface—Rose Bengal, Plate 25/2. Inner petal: Outside surface—Tyrian Rose, Plate 24/3; inside surface—Rose Bengal, Plate 25/2.

*General color effect.*—Newly opened flower—Rose Bengal, Plate 25/2. 3-days open—Solferino Purple, Plate 26/2.

*Behavior.*—Drop off clearly; not affected by weather.

*Flower Longevity.*—On bush in garden—5 days in June.

*Reproductive Organs*

Stamens: Many; regularly arranged about pistils. Color—Burnt-Orange.

Filaments: Medium length; most with anthers. Color—Yellow.

Anthers: Medium size; all open at once. Color—Brown.

Pollen: Moderate. Color—Gold.

Pistils: Many.

Styles: Uneven; medium length; medium caliper; very bunched.

Stigma: Color—Yellow.

Ovaries: All enclosed in calyx.

Hips: Pear-shaped; smooth; with thick walls. Color—Green.

Seeds: Many; large.

Sepals: Permanent; long; pear-shaped; recurved. Color—Bronze.

*Plant*

Foliage:

*Leaves.*—Compound of 5 leaflets; abundant; medium large; very heavy; leathery; glossy.

*Leaflets.*—Shape—ovoid, with apex acute. Base—round. Margin—doubly serrate.

*Color.*—Mature: Upper surface—Dark Green; under surface—Normal Green. Young: Upper surface — Normal Green; under surface —Normal Green.

*Rachis (the supporting stem of the compound leaf).*—Upper side—hairy. Under side—sparsely thorny.

*Stipules.*—Long; wide; with long points turning out at an angle of less than 45°.

*Disease resistance.*—Very resistant to mildew and blackspot, as compared with other varieties grown under comparable cultural conditions at Monroe, Michigan, U. S. A.

Growth:

*Habit.*—Bushy; upright.

*Growth.*—Very vigorous.

*Canes.*—Heavy.

*Main stems.* — Color — Dull Bronze. Thorns—many; medium length; hooked downward; with broad base. Prickles—none. Hairs—none.

*Branches.* — Color—Dull Green. Thorns—many; medium length; hooked downward; with broad base. Prickles—none. Hairs—none.

*New shoots.*—Color—Bright Bronze. Thorns—many; medium length; hooked downward; with broad base. Prickles—none. Hairs—nine.

I claim:

A new and distinct variety of rose plant of the hybrid tea class, substantially as herein shown and described, characterized particularly as to novelty by its hardiness, its leathery and glossy foliage, the fullness and distinctive color of its blooms and their habit of holding their color very well, and its very good resistance to blackspot and mildew.

No references cited.